(12) United States Patent
Benenson et al.

(10) Patent No.: US 11,021,761 B2
(45) Date of Patent: Jun. 1, 2021

(54) SCREENING ASSAY FOR IDENTIFYING MIRNA-SPECIFIC DRUG COMPOUNDS

(71) Applicant: ETH ZURICH, Zurich (CH)

(72) Inventors: Yaakov Benenson, Basel (CH); Benjamin Hafliger, Aarau (CH)

(73) Assignee: ETH ZURICH, Zurich (CH)

(*) Notice: Subject to any disclaimer, the term of this patent is extended or adjusted under 35 U.S.C. 154(b) by 0 days.

(21) Appl. No.: 15/316,488

(22) PCT Filed: Jun. 2, 2015

(86) PCT No.: PCT/EP2015/062258
§ 371 (c)(1),
(2) Date: Dec. 5, 2016

(87) PCT Pub. No.: WO2015/185551
PCT Pub. Date: Dec. 10, 2015

(65) Prior Publication Data
US 2018/0148799 A1 May 31, 2018

(30) Foreign Application Priority Data
Jun. 5, 2014 (EP) .................................... 14001958

(51) Int. Cl.
*C12Q 1/6897* (2018.01)

(52) U.S. Cl.
CPC ..... *C12Q 1/6897* (2013.01); *C12Q 2525/207* (2013.01); *C12Q 2545/101* (2013.01)

(58) Field of Classification Search
CPC .......................... C12Q 1/6897; C12Q 2600/178
See application file for complete search history.

(56) References Cited

U.S. PATENT DOCUMENTS

| 2010/0197006 | A1* | 8/2010 | Benenson | .............. | B82Y 10/00 435/325 |
| 2013/0005759 | A1* | 1/2013 | Deiters | .................. | A61K 31/04 514/296 |
| 2013/0023498 | A1 | 1/2013 | Huang | | |

FOREIGN PATENT DOCUMENTS

| WO | WO 2011/091209 A1 | 7/2011 |
| WO | WO 2012/012739 A2 | 1/2012 |
| WO | WO 2013/019469 A1 | 7/2012 |

OTHER PUBLICATIONS

Lee et al., The expression of the miRNA-200 family in endometrial endometrioid carcinoma, Gynecologic Oncology, vol. 120, pp. 56-62. (Year: 2010).*
Leisner et al., Rationally designed logic integration of regulatory signals in mammalian cells, Nature Nanotechnology, vol. 5, pp. 666-670. (Year: 2010).*
International Search Report and Written Opinion of the International Searching Authority, dated Jul. 6, 2015 for PCT/EP2015/062258, filed Jun. 2, 2015.
Kiranmai Gumireddy et al, "Small-Molecule Inhibitors of MicroRNA miR-21 Function", Angewandte Chemie International Edition, vol. 47, No. 39, Sep. 15, 2008 (Sep. 15, 2008), pp. 7482-7484, XP055198586, ISSN: 1433-7851, DOI: 10.1002/anie.200801555.
International Preliminary Report on Patentability, for PCT/EP2015/062258, dated Dec. 6, 2016.
Rinaudo, K. et al. A universal RNAi-based logic evaluator that operates in mammalian cells. Nat Biotech 25, 795-801 (2007).
Xie, Z., Wroblewska, L., Prochazka, L., Weiss, R. & Benenson, Y. Multi-Input RNAi-Based Logic Circuit for Identification of Specific Cancer Cells. Science 333, 1307-1311 (2011).
Nakabayashi, H., Taketa, K., Miyano, K., Yamane, T. & Sato, J. Growth of Human Hepatoma Cell Lines with Differentiated Functions in Chemically Defined Medium. Cancer Research 42, 3858-3863 (1982).
Lohmann, V. et al. Replication of Subgenomic Hepatitis C Virus RNAs in a Hepatoma Cell Line. Science 285, 110-113 (1999).
Coulouarn, C., Factor, V.M., Andersen, J.B., Durkin, M.E. & Thorgeirsson, S.S. Loss of miR-122 expression in liver cancer correlates with suppression of the hepatic phenotype and gain of metastatic properties. Oncogene 28, 3526-3536 (2009).
Kutay, H. et al. Downregulation of miR-122 in the rodent and human hepatocellular carcinomas. Journal of Cellular Biochemistry 99, 671-678 (2006).
Deal watch: GSK invests in targeting microRNA for the treatment of hepatitis C. Nat Rev Drug Discov 9, 350-350 (2010).
Landgraf, P. et al. A Mammalian microRNA Expression Atlas Based on Small RNA Library Sequencing. Cell 129, 1401-1414 (2007).
Mangan, S. & Alon, U. Structure and function of the feed-forward loop network motif. Proceedings of the National Academy of Sciences of the United States of America 100, 11980-11985 (2003).
Zhang, J.-H., Chung, T.D.Y. & Oldenburg, K.R. A Simple Statistical Parameter for Use in Evaluation and Validation of High Throughput Screening Assays. Journal of Biomolecular Screening 4, 67-73 (1999).
Weber, et al, PNAS, 105, 9994-9998, 2008.
Garzon, et al., Nat. Rev. Drug Discover, 9, 775-789, 2010.
Lindow & Kaup¬ipinen, The Journal of Cell Biology, 199, 407-412, 2012.
Young et al., J. Am. Chem. Soc., 132, 7976-7981, 2010.

* cited by examiner

*Primary Examiner* — Dana H Shin
(74) *Attorney, Agent, or Firm* — Bryan D. Zerhusen, Esq.; Nicholas R. Herrel, Esq.; Cantor Colburn LLP (57) ABSTRACT

The present invention relates to a method for identifying miRNA (microRNA)-modulating compounds by contacting a compound of interest with a cell comprising (i) a "miRNA-specific module" that reports specific miRNA target sequence binding by means of a first reporter product; (ii) a "non-specific RNAi module" that reports altered expression of one or more endogenous miRNAs with baseline expression levels in the cell ("non-specific miRNA markers") by means of a second reporter product; and optionally (iii) a "gene expression module" that reports global changes in gene expression; and subsequent detection of changes in reporter product expression. The advantage of this method is that non-specific miRNA- and/or RNAi-effects of the compound of interest are detected and false positive results due to the structural similarity of different miRNAs and the commonly shared maturation pathway for most miRNAs are substantially reduced over conventional miRNA screening assays.

18 Claims, 5 Drawing Sheets
(5 of 5 Drawing Sheet(s) Filed in Color)

Pilot circuit

Parallel circuit

Low markers feed-forward circuit

Complete feed-forward circuit

SCREENING ASSAY FOR IDENTIFYING MIRNA-SPECIFIC DRUG COMPOUNDS

RELATED APPLICATION

This application is a National Stage of PCT/EP2015/062258, filed: Jun. 2, 2015 titled: "SCREENING ASSAY FOR IDENTIFYING miRNA-SPECIFIC DRUG COMPOUNDS", which claims the benefit and priority to European Application No. 14001958.9, filed on Jun. 5, 2014, all of which are incorporated by reference in their entirety for all purposes.

FIELD OF THE INVENTION

The present invention relates to a method for identifying miRNA (microRNA)-modulating compounds by contacting a compound of interest with a cell comprising (i) a "miRNA-specific module" that reports specific miRNA target sequence binding by means of a first reporter product; (ii) a "non-specific RNAi module" that reports altered expression of one or more endogenous miRNAs with baseline expression levels in the cell ("non-specific miRNA markers") by means of a second reporter product; and optionally (iii) a "gene expression module" that reports global changes in gene expression; and subsequent detection of changes in reporter product expression. The advantage of this method is that non-specific miRNA- and/or RNAi-effects of the compound of interest are detected and false positive results due to the structural similarity of different miRNAs and the commonly shared maturation pathway for most miRNAs are substantially reduced over conventional miRNA screening assays.

BACKGROUND microRNA (abbreviated miRNA) is a small non-coding 19-25 bp long single-stranded RNA generated from hairpin-shaped transcripts and processed by nuclear and cytosolic proteins Drosha and Dicer. miRNA is found in plants, animals and some viruses and functions in transcriptional and post-transcriptional regulation of gene expression via base-pairing with complementary sequences within mRNA molecules. As a result, these mRNA strands are silenced and such complexes are often actively disassembled by the cell ("target degradation"). miRNAs are well conserved in eukaryotic organisms and are a vital and evolutionarily ancient component of genetic regulation. miRNA research has revealed multiple roles in negative regulation (transcript degradation and sequestering, translational suppression) and possible involvement in positive regulation (transcriptional and translational activation). By affecting gene regulation miRNAs are likely to be involved in most biological processes. This universality and the regulatory nature are also reflected in the frequency of miRNA involvement in diseases. The human miRNA disease data base (HMDD) reports the participation of more than 600 miRNAs in about 400 different diseases. Consequently, miRNAs are attractive drug targets but no miRNA-specific drug has reached the market yet.

Synthetic gene circuits are part of synthetic biology that addresses biological problems from an engineer's point of view. The synthetic systems have grown substantially to perform more complex operations in different cells such as bacteria, yeast and mammalian cells. The latest published gene circuits are designed to sense endogenous signals, compute with multiple inputs and produce specific responses, tailored to the situation in each cell (Xie et al., Science. 333, 1307-1311, 2011).

The first synthetic biology based screening assay was reported by Weber et al. in 2008, where a tuberculosis resistance gene was moved to mammalian cells, in order to detect modifiers of it (Weber et al., PNAS, 105, 9994-9998, 2008).

WO 2012/012739 A2 teaches a detector gene circuit for classifying a cell status based on detecting whether an input microRNA is expressed at a specific level or higher than a reference level. The gene circuit comprises (a) a constitutive or inducible promoter sequence operably linked to a repressor sequence encoding a repressor product and a sequence encoding one or more microRNA target sequences that target one or more input microRNAs that are to be detected; and (b) a repressible promoter sequence operably linked to an output sequence encoding a detectable output product, wherein said repressor product is specific for the repressible promoter sequence.

WO 2013/019469 A1 describes a screening assay for miRNA modulators, wherein a cell comprising a miRNA and a miRNA binding sequence operably linked to a nucleic acid encoding a reporter protein is contacted with a test agent and the effect of the test agent on the reporter protein is detected. A similar scre-ening test for miRNA modulators is taught in WO 2011/091209 A1, where a bidirectional luciferase reporter is used to detect miRNA target modulators. Both screening assays do not discriminate for a false-positive selection of modulators.

For therapy chemically synthetized miRNAs or miRNA analogues that either replace or inhibit natural miRNAs and second, miRNA level-modifying small molecules have been suggested (Garzon et al., Nat. Rev. Drug Discov., 9, 775-789, 2010). In this therapeutic approach miRNAs known for a certain disease are mimicked/inhibited and applied to the patient. Delivery, stability and pharmacokinetic profile of the compounds remain a challenge. Current first in class compounds are locked nucleic acids (LNAs), which are in phase II clinical trials (Lindow & Kauppinen, The Journal of Cell Biology, 199, 407-412, 2012). Alternatively, compound libraries are screened with cells harboring a miRNA target in its 3'UTR and using a reporter gene. Addition of the candidate compound should alter the expression profile of the reporter, thus indicating an effect on the respective miRNA (Young et al., J. Am. Chem. Soc., 132, 7976-7981, 2010; Gumireddy et al., Angewandte Chemie, Int. Ed., 47, 7482-7484, 2008).

The problem inherent to the presently available screening assays for miRNA targets is that there is a high chemical similarity of the different miRNAs and most of them share the same maturation pathway. In consequence, presently used screening assays lead to a substantial number of false positive screening hits with potentially adverse side effects. Currently, only a subset of the hits is tested in second round screenings, which results in high costs and the omission of possibly potent candidates.

SUMMARY

It is the object of the present invention to provide an improved screening assay for miRNA target sequences, in particular an assay that results in less false hits for the compounds screened. It is a further objective to provide a miRNA-specific assay that distinguishes between systemic and miRNA-specific effects and that preferably provides information on the absolute and relative magnitude of systemic and specific effects.

This object is solved by a novel cell-based screening method that com-bines (1.) the reporter output of a "miRNA-specific module" that indicates specific changes of the relevant miRNA level and/or activity induced by the compound of interest by reporting changes in the interaction of this miRNA with its target sequence, and (2.) the further reporter output of a "non-specific RNAi module" in the same cell that integrates changes in the activities of one or more endogenous miRNAs due to interaction with the compound of interest by modulating the activity of an integrating miRNA, the activity of which depends on the activity of one or more of the endogenous miRNAs.

In a preferred embodiment, the present invention is directed to a method for identifying miRNA (microRNA)-modulating compounds comprising the steps:

(A) providing a cell comprising
(i) at least one "miRNA-specific module" comprising a promoter sequence operably linked to at least one miRNA target sequence of interest and a nucleic acid sequence encoding a first reporter product;
(ii) at least one "non-specific RNAi module" comprising
  (a) a promoter sequence operably linked to one or more, preferably two or more target sequences for endogenous miRNAs with baseline expression levels in the cell ("non-specific miRNA markers") and
  (b) a promoter sequence operably linked to at least one target sequence for a miRNA (integrating miRNA) operably linked to a nucleic acid sequence encoding a second reporter product, wherein the activity of the integrating miRNA depends on the activity of the one or more of the non-specific endogenous miRNAs of (a) and/or on the activity of the RNA interference pathway in the cell,
(iii) optionally at least one "gene expression module" comprising a promoter sequence operably linked to a nucleic acid sequence encoding a third reporter product;
(B) contacting the cell of step (a) with a compound of interest under physiological conditions, and
(C) detecting
  (1) specific miRNA effects of the compound of interest on the specific RNAi module (i) based on changes in the expression of the first reporter product,
  (2) off-target and systemic RNAi effects of the compound of interest on the non-specific RNAi module (ii) based on changes in the expression of the second reporter product,
  (3) optionally non-specific effects of the compound of interest on the gene expression module (iii) based on changes in the expression of the third reporter product.

In a more preferred embodiment the at least one "non-specific RNAi module" (ii) comprises
(a) a promoter sequence operably linked to one or more, preferably two or more target sequences for endogenous miRNAs with baseline expression levels in the cell ("type I non-specific miRNA markers") and
(b) a promoter sequence operably linked to
(I) at least one target sequence for a miRNA (integrating miRNA), wherein the activity of the integrating miRNA depends on the activity of the one or more of the type I non-specific endogenous miRNAs of (a),
(II) one or more, preferably two or more target sequences for endogenous miRNAs with baseline expression levels in the cell ("type H non-specific miRNA markers"), and
(III) a nucleic acid sequence that encodes a second reporter product or that is operably linked to a second reporter product.

In a preferred embodiment the cell for use in the present invention may comprise a further nucleic acid sequence encoding a further reporter product for the purpose of internal normalization.

The method of the present invention leads to more robust results, less false-positive hits and overall much lower costs than conventional miRNA-screening assays because diverse off-target and systemic effects are integrated in a synthetic gene circuit, the so-called "non-specific RNAi module" and reported to confirm or deny target specificity. The gene circuit technology for integrating multiple miRNA input signals, in particular endogenous miRNA input signals, is illustrated in detail in WO 2012/012739 A2, a previous invention of one of the present inventors. The miRNA circuit technology taught in WO 2012/012739 A2 is included in this description by reference.

For easier analysis of the output results of the screening method of the present invention, it is preferred that the first, second and/or the optional third reporter products should be different.

The promoters in any of modules (i) to (iii) can be constitutive or inducible, preferably they are constitutive promoters. It is further preferred that the promoters in any of modules (i) to (iii) are different promoters.

In a preferred embodiment of the invention the "non-specific RNAi module" (ii) comprises two or more target sequences for endogenous miRNAs expressed at different expression levels, preferably at high and low expression levels.

Preferably the "non-specific RNAi module" (ii) for use in the invention comprises one or more target sequences for endogenous miRNAs selected from the group of low miRNA expression level target sequences miR-200c, 145, 141, 375, 146a and/or from the group of high miRNA expression level target sequences miR-21, 17, 130a and 20a. In a more preferred embodiment the "non-specific RNAi module" (ii) comprises at least one, preferably at least two or more target sequences for endogenous miRNAs selected from the group of low miRNA expression level target sequences miR-141 and miR-146a and/or from the group of high miRNA expression level target sequences miR-21 and miR-20a. Most preferred the "non-specific RNAi module" (ii) comprises at least one or both target sequences for endogenous miRNAs miR-141 and miR-146a in combination with at least one or both target sequences for endogenous miRNAs selected from the high miRNA expression level target sequences miR-21 and miR-20a.

In a further preferred embodiment the expression of the second reporter product in the "non-specific RNAi module" (H) is controlled by two or more proportional and inverse miRNA target sequences for different miRNAs. Illustrating examples of proportional and inverse miRNA target sequences miRNAs are described further below.

The method of the invention can be practiced with any cell that can be modified to functionally comprise at least the above-described modules (i) and (ii), preferably modules (i) to (iii). The cells can either naturally produce the miRNA of interest or it can be manipulated to do so. It is preferred that the cell for practicing the present invention is a disease model cell, preferably a cancer cell, more preferably an HCV model cell, most preferably a HuH-7 cell.

In a more preferred embodiment, the miRNA of interest is miRNA-122 and the corresponding specific miRNA target sequence in the at least one "miRNA-specific module" (i) binds specifically to miR-122.

In a preferred embodiment of the present invention at least one of the reporter products in the "miRNA-specific module" (i), the non-specific RNAi module" and/or the "gene expression module" (iii) is a fluorescent protein or luciferase, preferably selected from the group consisting of mCitrine fluorescent protein, mCherry fluorescent protein, ZsYellow fluorescent protein, and mCerulean fluorescent protein.

In the following the method of the present invention will be illustrated by specific examples and figures, none of which are to be interpreted as limiting the scope of the present invention beyond the scope of the appended claims.

The cells, e.g. HuH-7 cells, the design of the modules (i) to (iii) as described above generally and specifically below, in particular the circuit design(s) of the "non-specific RNAi module" and the specific embodiments such as promoters, bidirectional promoters, repressors, activators, proportional and inverse miRNA target sequences, reporter proteins, etc. as described below are not to be interpreted as limiting the illustrated concepts of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 (a) is a high-level representation of the screening assay of the present invention. Three different modules identify different types of perturbbations.

FIG. 1 (b) is a schematic representation of the fluorescent (top) and luciferase based (bottom) reporter systems used for testing the activity of different endogenous miRNAs. A constitutive driven transactivator (TA) is used to activate the bidirectional reporter system composed of an untargeted internal control (mCerulean, Firefly Luc) and a targeted reporter for the miRNA knockdown readout (mCherry, Renilla Luc). Tx denotes four repeats of the inverse complement of minx sequence.

FIG. 1 (c) is a graph showing relative reporter levels for different miRNAs in HuH-7 cells. Bars are arranged according to the knockdown strength of the miRNAs, from inactive (left) to potent (right). The bar charts show mean±SD for biological triplicates.

FIG. 2 illustrates the initial characterization and fine-tuning of circuit components.

FIG. 2 (a) is a blueprint of the circuit that fits the abstract representation in FIG. 1a. DNA, RNA and Proteins are lumped together. Dark grey circles represent rtTA, brown ones pTRE-LacI-ˆmiR-FF4ˆ and yellow-grey one is mCitrine linked to a transactivator. Brightly-colored circles represent various fluorescent reporters.

FIG. 2 (b) shows a dose-response of pTRE-driven fluorescent reporter to varying amounts of rtTA furnished with different miRNA targets, as indicated. FF5 is a scrambled miRNA target and it results in the strongest possible dose-response.

FIG. 2 (c) shows a dose-response of newly constructed bidirectional reporters to varying amounts of theft cognate activators, as indicated in the panel. rtTA dose-response is shown for comparison.

FIG. 2 (d) depicts a comparison of knockdown efficiency of miRNA mimics on two different transactivators with different positioning of the respective targets, as indicated. Yellow bars represent the direct readout of the targeted protein (mCitrine). Blue bars indicate the expression of fluorescent reporter controlled by this transactivator via a bidirectional promoter.

FIG. 2 (e) illustrates the optimization of high-marker sensor composition in HuH-7 cells. Response of the transactivator output (mCitrine) and the downstream mCerulean output is measured with varying amounts of high marker sensor genes, separately for miR-21 and miR-20a sensors. Sensor genes furnished with scrambled FF5 target sequence generate baseline "Off" response. All data points and bars shown are mean±SD of biological triplicates.

FIG. 3 illustrates the design and evaluation in silico and in experiments of four assay architectures.

FIG. 3 (a) is a schematic representation of different circuit topologies. The sensor genes for two high markers are common to all designs. The components that differ are framed and labeled. Dependent on the design, different fluorescent proteins serve as module outputs.

FIG. 3 (b) depicts the experimental characterization of the Pilot Circuit using small number of non-specific marker modulators. Bars show means±SD of biological triplicates FIG. 3 (c) illustrates a sample of simulation results showing how different circuits respond to changes in parameter values, here the total cytoplasmic concentration of RISC complexes in units of molecules per cell (mpc).

FIG. 3 (d) shows the simulated dependency of the non-specific RNAi module output on changes in total RISC as well as processing efficiency of miR-FF4. The high markers are set at 1000 mpc each and the low markers at 5 mpc each.

FIG. 3 (e) is a comparison of the different circuit layouts under different perturbations of non-specific markers, miR-122, and miR-FF4. Top panel shows non-specific output changes with 13 relevant conditions. Gray boxes enclose values measured with control samples (scrambled mimic and LNA). Bottom panel displays changes in the specific output after two relevant perturbations. The worst-case fold-change difference is shown. All data points are mean values of biological triplicates.

FIG. 4 illustrates an in-depth characterization of OFF circuit.

FIG. 4 (a) shows quantitative data measured with 15 different perturbations. The table describes the perturbations, which are numbered from 1 to 15. Each column shows which miRNA/s are changed relative to HuH-7 background (gray columns). "−1" indicates LNA inhibitor and "+1" indicates transfection of miRNA mimic. Performance was accessed using flow cytometry (bar charts) with representative images shown on top. Faint blue and red bands illustrate the range in which the changes of mCerulean and mCherry outputs, respectively, are considered insignificant. Gray columns indicate control measurements (nothing added, scrambled LNA, and scrambled siRNA, from left to right) and the numbers represent idealized marker levels in HuH-7 cells. Pink columns emphasize specific modulation of miR-122.

FIG. 4 (b) shows the results of testing of dose-response to gradual increase of perturbations corresponding to the 15 states shown in (a). Pale blue and red lines represent the behavior with the corresponding controls. The controls were measured with varying amount of scrambled LNA for miRNA inhibition experiments, and varying amounts of scrambled mimic for miRNA activation experiments. The dose response curves were fitted with exponential functions to serve as a visual guide. All bars and data points are mean±SD of biological triplicates.

FIG. 5 (a) is a schematic representation of the small molecule screen performed. Red dots indicate control wells.

See Methods for details on Statistical Analysis. All hits were visually inspected in order to identify possible measurement artifacts.

FIG. 5 (b) shows results of data analysis from the screen, with each point representing the mean of a biological triplicate measurement (no error bars shown). The yellow and green-colored dots represent compounds that induced statistically significant changes in non-specific outputs relative to reference distributions with a p-value of 0.1 or less. These compounds were excluded due to high probability of non-specific interactions. Compounds were first excluded based on mCitrine output, then based on mCerulean/mCitrine ratio. Therefore, the number of compounds is reduced from left to right. The red dots on the right-hand plot indicate the hits whose mCherry/mCitrine ratio differs significantly from the reference distributions with a p-value of 0.01 or less. Red lines indicate mean+SD and mean−SD of the reference distributions, added as visual guides.

DETAILED DESCRIPTION

Introduction

In the following an assay for selective modulators of miR-122 in HuH-7 cells is described. The below described three modules report, respectively, on global changes in gene expression, non-specific microRNA and/or RNAi effects, and specific targeting of miR-122. The assay was validated using artificially induced changes in various microRNA levels and was used to screen a library of about 400 chemicals, thereby identifying a number of potential hits and discarding multiple compounds with off-target effects.

Figure 1A:
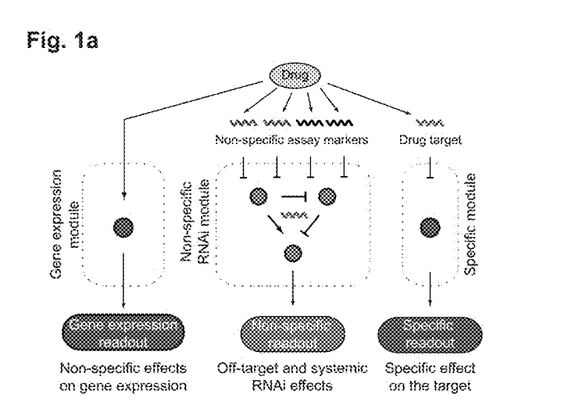

On a high level of abstraction, the assay described below consists of three modules that generate three fluorescent outputs, or readouts, representing, respectively, a non-specific systemic effect on gene expression; a non-specific effect on unintended miRNAs and/or systemic effect on the RNAi pathway; and a specific effect on the miRNA of interest (FIG. 1a). The first one called "Gene expression module" generates fluorescent output from a constitutive expression cassette that also serves as a normalization control. The second, called "Non-specific RNAi module", samples a subset of endogenous miRNAs with characteristic baseline expression levels in the assay cell line ("non-specific assay markers"), including both high ("high markers") and low expression ("low markers"); it also contains a synthetic miRNA whose activity depends on systemic RNAi parameters. The output of this module, the "non-specific readout" is high when marker levels are unaffected, and it changes when off-target activity of a drug candidate modulates marker levels or affects RNAi pathway non-specifically. The third circuit module called "Specific module" reports the activity of a compound on the miRNA of interest: its output ("specific readout") reflects the magnitude of the desired specific effect and its direction.

Methods

Plasmids Construction.

Plasmids were constructed using standard cloning techniques. E. coli DH5α was used as the cloning strain, cultured in LB Broth Miller Difco (BD) supplemented with appropriate antibiotics (Ampicillin. 100 µg/ml, Chloramphenicol, 25 µg/ml, Kanamycin, 50 µg/ml). All enzymes were purchased from New England Biolabs (NEB). Phusion High-Fidelity DNA Polymerase (NEB) was used for fragment amplification. Single stranded oligonucleotides used as primers or for annealing were provided by Microsynth or Sigma-Aldrich. Digestion products or PCR fragments were purified using GenElute Gel Extraction Kit or Gen Elute PCR Clean Up Kit (both Sigma-Aldrich). All ligations were performed using T4 DNA Ligase (NEB) with individually adjusted incubation time and temperature, following transformation into chemically competent E. coli DH5α and plating on LB Agar plates with appropriate antibiotics. Clones were analyzed by colony-PCR using Quick-Load Taq 2× Master Mix (NEB) or by test restriction after Miniprep purification of plasmids of individual clones using GenElute Plasmid Miniprep Kit (Sigma-Aldrich). All plasmids were sequenced by Microsynth.

Cell culture and transfection.

HuH-7 cells were received from the Health Science Research Resources bank of the Japan Health Sciences Foundation (Cat-# JCRB0403, Lot-#07152011) and cultured at 37° C., 5% CO2 in DMEM, low glucose, GlutaMAX (Life technologies, Cat #21885-025), supplemented with 10% FBS (Sigma-Aldrich, Cat #F9665 or Life technologies, Cat #10270106) and 1% Penicillin/Streptogamine Solution (SigmaAldrich, Cat #P4333). Splitting was performed every 3-4 days using 0.25% TrypsinEDTA (Life technologies, Cat #25200-072). Transfection was performed using Lipofectamine 2000 Transfection Reagent (Life Technologies. Cat-#11668-019) in uncoated 24-well plates (Thermo Scientific, Cat-#142475), 96-well plates (Thermo Scientific, Cat-#167008) or black µ clear 96-well plates (Greiner bio-one, Cat-# 655090). For transfections in 24 well plates HuH-7 cells were seeded one day before transfection at a density of 65,000 cells/well in 500 µL complete medium. The medium was replaced before transfection with medium supplemented with Doxycycline hyclate (Fluka, Cat # 44577) at a final concentration of 1 µg/mL. For 96-well plates, transfection was performed in suspension. Specifically, HuH-7 cells were seeded at a density of 30,000 cells/well in 100 µL in complete medium supplemented with Doxycycline hyclate (Fluka. Cat #44577) at a final concentration of 1 µg/ml right before transfection (Suspension transfection protocol from the manufacturer). Transfections were performed at 80-90% cell confluence. Plasmids were purified from 100 mL-400 mL cultures of E. coli DH5a grown overnight at 37° C. at 200 rpm in LB Broth Miller Difco (BD) supplemented with appropriate antibiotic using HiPure Plasmid Filter Maxi Kit (Invitrogen) or PureYield Plasmid Midiprep Kit (Promega). After plasmid purification an additional purification step was performed using Endotoxin Removal Kit (Norgen Biotek Corporation). DNA amounts were quantified using Nanodrop (ND-2000) and integrity was verified by agarose gel electrophoresis. The purified plasmids were mixed and diluted with 50/25 µL Opti-MEM I Reduced Serum (Gibco, Life technologies Cat #31985-962) per sample for 24/96-well plates respectively. If needed, microRNA mimics, siRNAs and LNA-inhibitors were added to the plasmid mix. Mimics were purchased from Thermo Scientific (Mim-20a Cat # C-300491-03, Mim-21 Cat # C-300492-03-0005, Mim-122 Cat # C-300591-05, Mim-141 Cat # C-300608-03, Mim-145 Cat # C-300613-05, Mim-146a Cat-# C-300630-03, Mim-375 Cat-# C-300683-05, Mim-Neg.Ctrl. Cat # CN-001000-01-05), siRNAs from Microsynth (siFF4, siDicer, siNegCtrl—all custom order) and LNA inhibitors form Exiqon (LNA-20a Cat #426943-00, LNA-21 Cat #426947-00, LNA-122 Cat #426674-00, LNA-FF4 (custom order), LNA-Neg.Ctrl. Cat #199020-00). Lipofectamine 2000 was used at a Lipofectamine [µL]: DNA [µg] ratio of 1:2.5 and was mixed with 50/25 µl Opti-MEM for 24/96-well plates respectively. After 5 minutes incubation at room temperature, the diluted Lipofectamine was mixed with the diluted DNA sample. The mixture was incubated for 20 min at room temperature and added to cells.

Drug Screening.

Small molecules were received through the NIH Clinical Collection program via Evotec. 727 compounds were shipped in 96-well plates. 10 mM in 50 µL DMSO, of which a subset of 361 were screened. Purity was guaranteed by supplier. Dilutions were first performed in DMSO to 1 mM and afterwards in complete medium to 30 µM. 50 µL of this compound medium was added to the screening plates. The circuit transfection was prepared in bulk as described above and added to the compound-containing medium, resulting in a final concentration of 10 µM compound and 1% DMSO. Positive and negative controls were placed in rows 1 and 12, containing untransfected cells, pure DMSO, 5 nM LNA-122, 5 nM Minn-122. 5 nM LNA-21 and 5 nM Mim-146a. Cells were assayed after 48 h using microscopy as described below. Data processing is described below.

Fluorescent Microscopy.

Fluorescent images were generated 48 hours after transfection by an inverted Fluorescent Microscope (Nikon Eclipse Ti) using a Fiber Illuminator (Nikon Intensilight C-HGFI), optimized optical filter sets (Semrock) and a Digital Camera System (Hammamatsu, ORCA R2). The filter sets contain an optimized combination of excitation band pass filter, emission band pass filter and a dichroic filter for each individual fluorescent protein. We measured mCerulean, mCitrine, mCherry and iRFP with the filter set CFP HC (HC 438/24, HC 483/32, BS 458), YFP HC (HC 500/24, HC 542/27, BS 520), TxRed HC (HC 624/40, HO 562/40, BS 593), Cy5.5-A (HC 655/40, HC 716/40, BS 685)), respectively. The acquired images were uniformly contrast-enhanced for better visualization by ImageJ software.

Flow Cytometry.

Samples were analyzed 48 hours after transfection by a BD LSR Fortessa cell analyzer. The medium was removed and cells were incubated with 150/50 µL phenol-red free Trypsin (0.5% Trypsin-EDTA (Gibco, Life Technologies, cat #15400-054) 1:2 diluted with PBS (Life Technologies cat #10010-56). Dispersed cells were transferred to FACS tubes (Life Systems Design, Cat #02-1412-000) and kept on ice. For the detection of the different fluorescent reporters we used reporter-specific combinations of excitation lasers and emission filters. For mCherry we used a 561 nm excitation laser 600 nm Longpass filter and 610/20 emission filter. For mCitrine we used 488 nm Laser, 505 nm Longpass filter and 542/27 nm emission filter. For mCerulean we used a 445 nm Laser and a 473/10 nm emission filter. For iRFP, we used a 640 nm Laser and 780/60 emission filter. PMTs were adjusted using standard fluorescent beads before and after each measurement in order to maintain constant device performance.

Luciferase.

Cells were harvested 48 h post transfection. Supernatant was removed, cells were washed with PBS and 100 µL 1× passive lysis solution (Promega) was added (Incubation at 37 for 15 min). The luciferase reaction was performed using Promega's dual luciferase assay kit. We mixed 20 µL of lysed cells with 50 µL of respective reagent. Measurement was performed with a lag time of 2 s and 10 s recoding time using Sirius instrument (Berthold Detection Systems).

Flow cytometry data and image processing.

All flow cytometry data were analyzed using FlowJo software. Compensation of minor crosstalk (<1.8%) of mCerulean into the 488-542/27 nm channel and of mCherry in 640-780/60 nm channel was performed if necessary using single color controls. The values in the bar charts, shown as relative expression units (rel.u.) are calculated as follows. (i) Live cells are gated based on their forward and side scatter readouts. (ii) Within this gate, 99.9% of the cells of the negative control fall into the negative bin for each color. (iii) For each positive cell population in a given channel, the mean value of the fluorescent intensity is calculated and multiplied by the frequency of the positive cells. This value is used as a measure for the total reporter signal in a sample. The total reporter signal of an output was normalized with the total signal of the transfection control fluorophore to counterbalance possible transfection variation. The procedure can be summed up in the following formula:

Reporter intensity in rel.u.=[mean(Reporter in Reporter+cells)*Frequency (Reporter+cells)]/ [mean (Transfection Control Fluorophore in Transfection Control Fluorophore+cells)*frequency (Transfection Control Fluorophore+ cells)].

Drug screening data of FIG. 5 was processed as follows: All microscopy images were exported as tiff-files using MS-Elements Viewer's "Export" function. All images were cropped by 10 pixels on each side, in order to get rid of stitching artifacts. The background image for each plate in mCerulean and mCitrine channels was calculated by individual averaging of image pixels from non-transfected wells A1 and H12. Then, we subtract (pixel-by-pixel) these averaged background image files from all other images of the same plate and finally calculate the average intensity of the background-corrected image. For mCherry, after cropping we first applied MATLAB's msbackadj function ('Window-size', 130) row wise for all images, including non-transfected wells A1 and H12, thus performing the first round of background correction. In the second step the background image for each plate was calculated by averaging each pixel of previously-corrected mCherry snapshots from non-transfected wells A1 and H12. Finally we subtracted these averaged background images, pixel-by-pixel, from all other previously-corrected mCherry images in the same plate thus performing an additional round of background correction. Lastly, each corrected mCherry image is integrated and average intensity is used as the readout. The resulting mCerulean and mCherry values were individually normalized with their corresponding mCitrine values.

Statistical Analysis.

Figure 5A:
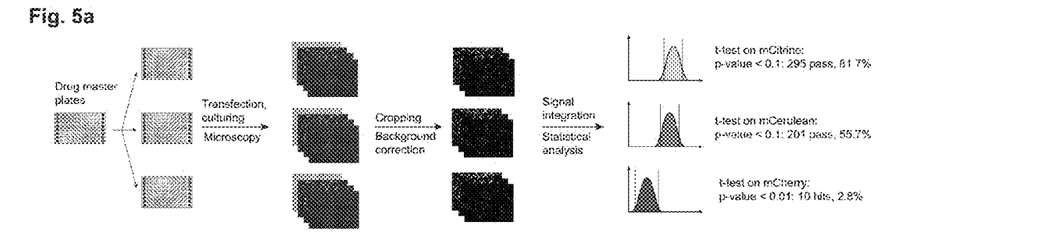

Ave compound storage plates were used in the screen, with about 80 compounds in each plate. Each plate was "replicated" three times for the screening assay, and each compound assayed as a triplicate in 3 different plates. Triplicate assay plates belonging to separate storage plates were analyzed separately. For mCitrine, absolute readouts were compared, while both mCerulean and mCherry readouts were internally normalized to mCitrine values in each well. The set of measurements made with all compounds in a given storage plate (about 240 values in total for each readout) was used as a reference distribution for individual compounds from this plate for the purpose of exclusion and hit identification 50. Specifically, a triplicate measurement of each compound was compared against its respective reference distribution using a two-sided t-test. Compounds that generated non-specific mCitrine and normalized mCerulean readouts that differed from the reference with a p-value of 0.1 or less, were considered as potential non-specific modulators and thus were excluded from the analysis. Compounds that generated normalized mCherry readouts that differed from the reference distribution with p-value of 0.01 or less, were classified as hits (FIG. 5a). In order to test whether the data used in the t-test are distributed normally, we built histograms of readouts and fitted them to normal distribution using histfit MATLAB function.

Modeling.

Model was built and simulations performed using MATLAB and SimBiology toolbox. All simulations were performed with "sundials" solver, with 10-6 absolute and 0.001 relative tolerance. The endpoint of the simulation was chosen at 50 hours. Parameter scans were performed with MATLAB code executing the SimBiology model in a loop using sbiosimulate command with different parameter values. Endpoint values were used for analysis.

Choice of Experimental System

As a proof-of-concept HuH-7 cells were used as the assay cell line and miR-122 as the drug target. HuH-7 is a well-differentiated liver cancer cell line used as a liver tumor model40 and as a model of HCV infection (41). Studies showed association between miR-122 and liver cancer (42, 43). In addition, HCV life-cycle depends on high levels of miR-12244. These properties make miR-122 a promising drug target (45).

Figure 1B:
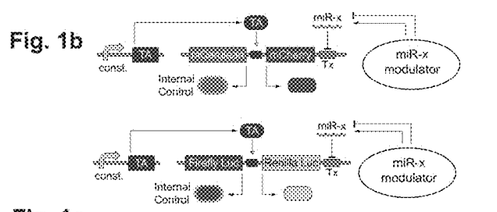
Figure 1C:
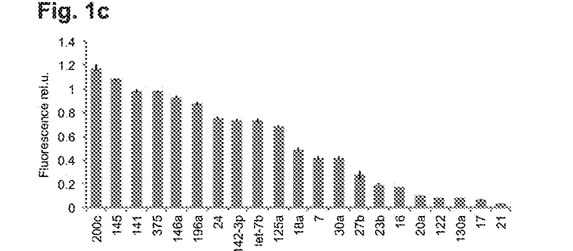

In order to identify non-specific assay markers, miRNAs expressed at either high or low level were sought in order to maximize the sensitivity of the non-specific readout (see below). Therefore, 21 candidate miRNAs were chosen based on reporter expression data (46), and bidirectional reporters were designed (FIG. 1b) and furnished with their targets to measure endogenous miRNA activity in HuH-7 cells (FIG. 1c). The promising candidates for non-specific low-level markers were miR-200c, 145, 141, 375 and 146a; and miR-21, 17, 130a and 20a for the high-level ones.

Candidates for assay validation purposes were synthetic miRNA mimics and LNA-based miRNA inhibitors. All mimics used showed good performance, with miR-146a and miR-141 mimics slightly outperforming miR-145 and miR-375. Therefore, miR-141 and miR-146a were chosen as the low marker inputs for the non-specific RNAi module. Likewise, LNAs against miR-21 and miR-20a resulted in almost-complete inhibition of their cognate miRNAs. To verify that the mimics and the LNAs can be used together to simulate different non-specific effects, their mutual orthogonality was also measured, whereby each mimic or LNA was tested with all the reporters including their cognate ones. The data showed that there was no significant crosstalk within this set.

Initial Design and Fine-Tuning of the Assay Circuit

At the initial design stage, a single gene comprising fluorescent protein driven by a constitutive promoter was chosen as the gene expression module. For the non-specific RNAi module, it was decided to adapt to HuH-7 cells by a previously reported approach for multiple miRNA marker integration (5, 15) (See also circuit diagrams in FIGS. 2e and 3a for details) whereby a particular pre-defined marker expression profile results in high protein output while deviations from this profile lead to changes in output, either downwards or upwards depending on the perturbation (see below). Very briefly, protein output is controlled simultaneously by a number of proportional and inverse miRNA sensors for individual markers. The former promote output expression when the sensed miRNA is highly expressed, while the latter down-regulate the output when the corresponding marker is high. The relationship between the sensed miRNA markers and the output is approximated by the logic equation Output=(High marker 1) and (High marker 2) and . . . and NOT (Low marker 1) and NOT (Low marker 2) and NOT ( . . . ) . . . .

Figure 2A:
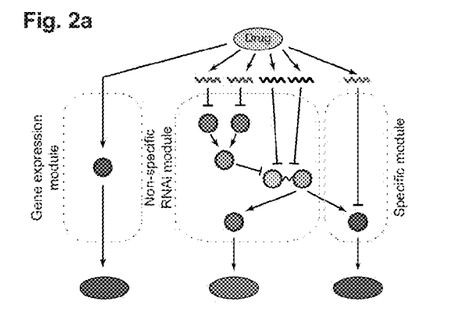

To measure specific effects on miRNA target of interest, a fluorescent reporter furnished with a tandem repeat of a sequence fully complementary to miR-122 in its 3'-UTR was chosen. An interface between the non-specific and specific modules via a transcriptional regulator was also planned (FIG. 2a).

Figure 2B:
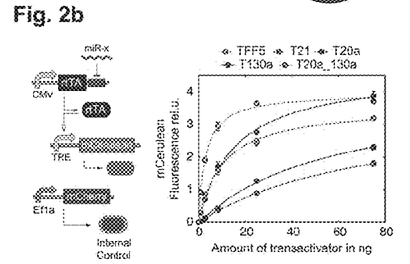
Figure 2C:
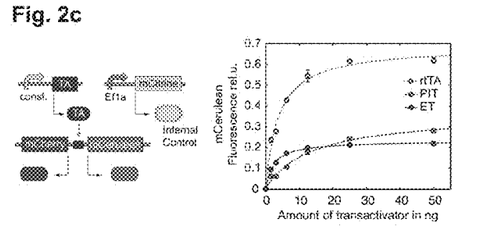

Experimental construction commenced with the optimization of individual sub-circuits in the various modules, as follows. First, the high-level sensors were calibrated and it was found that miR-21 and miR-20a, but not the miR-130a or composite miR-20a-130a markers, could be sensed successfully (FIG. 2b). Second, an interface was constructed between the non-specific and specific circuit modules that comprises a transactivator regulating a bidirectional promoter driving two fluorescent reporters. Since rtTA is used in high marker sensors (15), the known engineered transactivators PIT247 and ET48 were used and appropriate bidirectional promoters were constructed. Both performed comparably to well-characterized rtTA-pTRE-bi combination (FIG. 2c) and both activators were used in the next round.

Figure 2D:
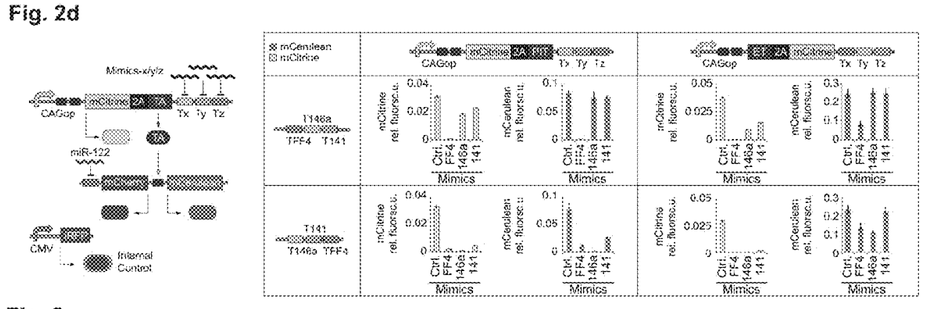
Figure 2E:
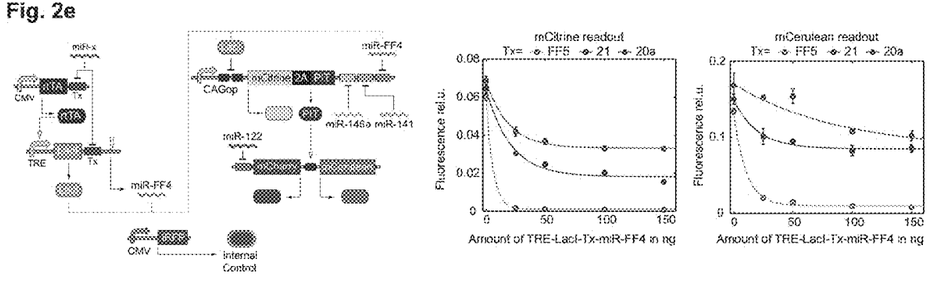

Next, PIT2 and ET were employed as outputs of a non-specific RNAi module: they were fused with mCitrine fluorescent protein via 2A linker, placed under the control of CAGop and furnished with the target sequences of low-expressed HuH-7 markers miR-141 (T141) and miR-146a (T146a) as well as the target sequence of miR-FF4 used in high maker sensors (TFF4). First, the knockdown of either PIT2 or ET by miRNAs directed against their 3'-UTR as well as the reduction in the protein levels driven by bidirectional promoter was measured. It was found that the order of target sequences in the 3'-UTR had a dramatic effect on the knockdown efficiency, with the best-performing arrangement containing TFF4 downstream of T141 and T146a (FIG. 2d). Only PIT2 enables reliable knockdown propagation via the bidirectional promoter (FIG. 2d). Secondly, similar measurements were made using the sensors for high markers miR-21 and miR-20a and varying the amount of sensor genes. A satisfactory On:Off ratio both on the activator and the downstream reporter level was observed and the optimal plasmid composition was identified (FIG. 2e).

Testing of Pilot Circuit and Comparison of Different Circuit Topologies

Figures 3A, 3B:
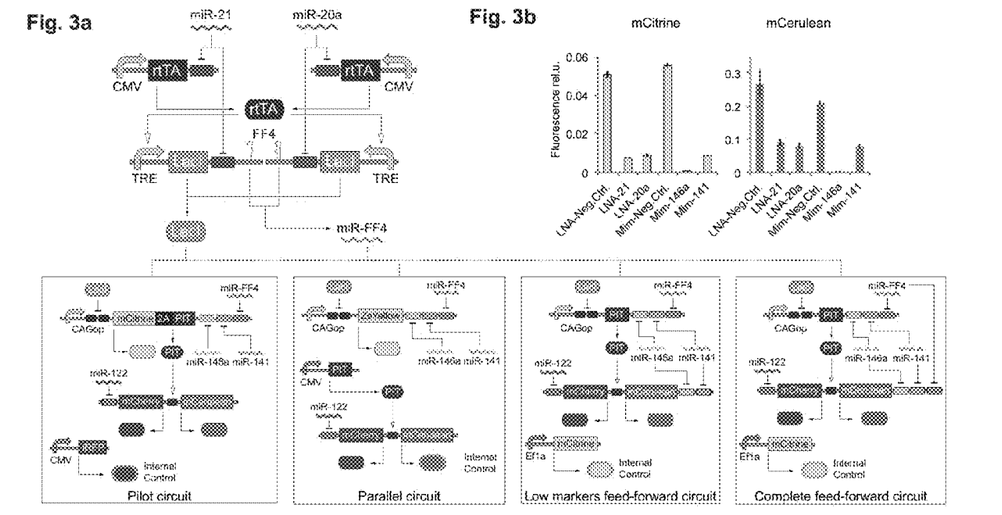

At this stage, all circuit parts were optimized individually and their respective ratios determined. The fully assembled "Pilot circuit" (FIG. 3a) receives five different miRNA inputs, of which four feed into the non-specific RNAi module. It was investigated whether changes in individual non-specific assay markers are reliably reported by this module using LNA and miRNA mimics to alter their levels. It was found that the dynamic range for all markers is good on mCitrine-2A-PIT2 level but it deteriorated quickly downstream for both high and low marker modulation (FIG. 3b), also when compared to observation in FIG. 2e. It was concluded that the Pilot circuit performance was not satisfactory for a robust assay and considered alternative topologies of both more and less modular architectures. Fully modular architecture is called "Parallel circuit", in which specific and non-specific modules are separated by severing the transactivator link. Thus, changes in mCitrine (replaced here with ZsYellow protein) can be directly used as the non-specific readout and mCherry can be normalized to coexpressed mCerulean. In the architectures with higher degree of connectivity, miRNAs that target the PIT2 activator in the Pilot circuit also target PIT2-induced Cerulean output. It was reasoned that this incoherent feed-forward motif (49) would improve the dynamic range of mCerulean compared to that observed with PIT2 in the Pilot circuit and ZsYellow in the Parallel Circuit, much like the structure of the high marker sensor (15) benefited from similar arrangement between rtTA and LacI. The first such layout called "low markers feed-forward circuit" (LM-FF circuit) employed low markers only; the second, called "complete feed-forward circuit" (CFF circuit) included feed-forward motifs by low markers and miR-FF4 (FIG. 3a). In both feed-forward circuits, mCerulean could no longer serve as an internal reference for miR122 knockdown of mCherry. Therefore, mCitrine was disconnected from the PIT2 activator and placed under constitutive EF1a promoter to serve both as the readout of gene expression module and as an internal normalization control for mCherry knockdown.

Figure 3C:
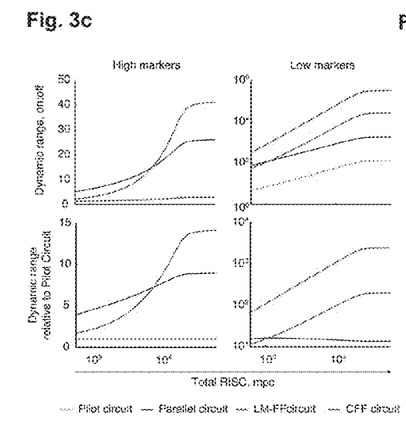

To explore these designs in silica a complete mechanistic model was implemented that could be adjusted to represent each of the four architectures with small changes in its reaction networks. There are two related sources of non-specific effects. First, change in unintended miRNA levels and/or activities for any number of reasons. Second, global changes to RNAi machinery. To simulate circuit response to changes in non-specific marker levels, the dynamic range was calculated by altering, in the model, high and low miRNA marker concentrations. With high markers, it was concluded that Parallel and CFF architectures are greatly superior to the rest, and that under wide range of parameter values. CFF circuit is superior to the Parallel circuit with 2-3 fold improvement. This improvement is expected when RNAi-related parameters reflect fast and efficient down-regulation such as high levels of RISC complex, low KM value for loaded RISC toward its target mRNA, and high kCAT of mRNA degradation/se-questration (FIG. 3c). With low markers, LM-FF circuit is superior to all others with very high dynamic range. CFF circuit is second best, while still performing well.

Figure 3D:
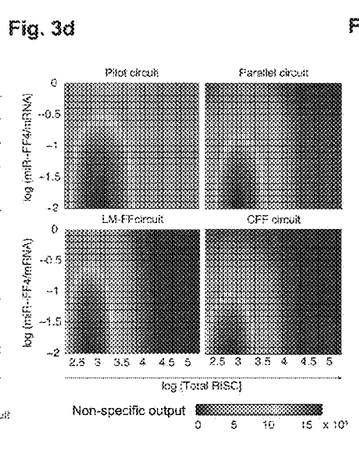

Global changes to RNAi machinery are unlikely to affect KM and kCAT values because these represent basic biochemical properties of the pathway; instead the likely changes will affect the total amount of RISC complexes or the efficiency of miRNA processing. RISC concentration is a parameter in the model; for miRNA processing, the fact was used that a synthetic miR-FF4 is spliced from LacI^FF4^ pri-mRNA. It was reasoned that the ratio between the amount of processed LacI mRNA and the mature miR-FF4 is a good proxy for global changes in miRNA processing and maturation pathway. Changes were mapped in circuit output as a function of RISC concentration and miR-FF4/LacI mRNA ratio (FIG. 3d). Once again, Parallel and OFF circuit are superior to the other two architectures in terms of sensitivity to change; because the mCerulean output contains a target for miR-FF4, CFF is more sensitive than Parallel circuit. Thus the simulation supported expectations and pointed to OFF as an optimal architecture; since the exact parameter values are unknown, it was decided to test all of them experimentally.

Figure 3E:
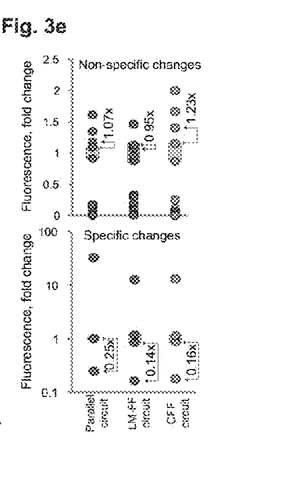

A set of 15 measurements was designed that included perturbations of individual miRNAs via LNA or mimics, as well as simultaneous changes of their subsets either toward higher or lower activity (for details see the Table next to the bar chart in Ag. 4a). Individual up- or down-regulation of four non-specific markers, miR-FF4 and miR-122 gives 10 perturbations in total, shown as conditions 1-4 and 7-12 in the Table in FIG. 4a (miR-141 and miR-146a were not tested with LNAs because they were already very low). Five additional conditions represent various simultaneous alterations of the miRNAs. In order to differentiate the architectures, the concept of "best-worst-case" was applied because the system's weakest link defines its overall performance. Two of the 15 perturbations (miR-122 mimic and LNA-122) reflect the dynamic range of the specific module, and the rest of the non-specific one. Thus, the specific mCherry and non-specific mCerulean readouts were evaluated in these respective cases and compared with the control samples. The resulting plots for the former were gathered in FIG. 3e (bottom panel), and the latter in FIG. 3e (top panel). It was found that OFF circuit generated larger scatter of readouts in non-specific scenarios, reflecting higher sensitivity as predicted by the model. Importantly, the worst case was observed with LNA-FF4 and yet it was detectable. Two other architectures showed lower sensitivity to FF4 down-regulation. This is important, because FF4 is a key reporter of systemic RNAi changes. As expected, feed-forward motif involving miR-FF4 made a circuit sensitive to those changes. In the specific module, both feed-forward networks were similar to each other and superior to Parallel circuit even though the reason is unclear. Based on the entire dataset, the CFF architecture was chosen as the leading assay circuit. In addition, it generated robust fluorescent readouts in HuH-7 cells.

Figure 4A:
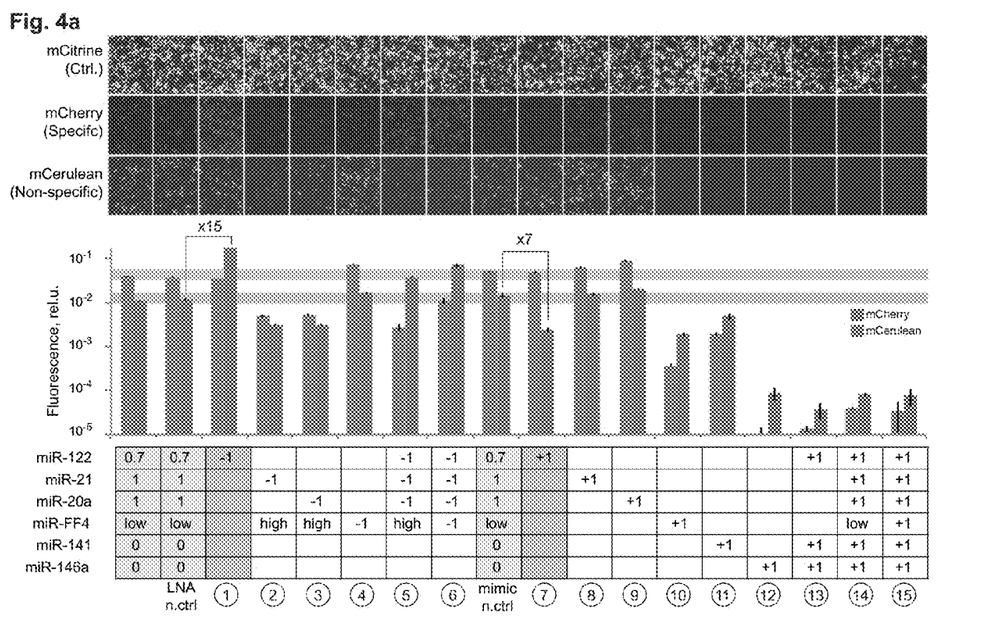

The detailed summary of CFF circuit behavior with 15 conditions as well as representative images from cell culture are shown in FIG. 4a. In specific cases it was observed that the induction of miR-20a and miR-21 and the inhibition of miR-FF4 generated smallest (yet substantial) effects on the non-specific RNAi module output, corresponding to the three readouts in FIG. 3e that are above the controls. Simultaneous up-regulation of all non-specific markers is another interesting case, because the effects on the readout from high and low markers are counteracting. In measurements corresponding to these cases, it was observed that the effects of increasing low markers always override those of high markers since the output sensitivity to low markers is much higher.

In-Depth Characterization of Complete Feed Forward Circuit

Figure 4B:
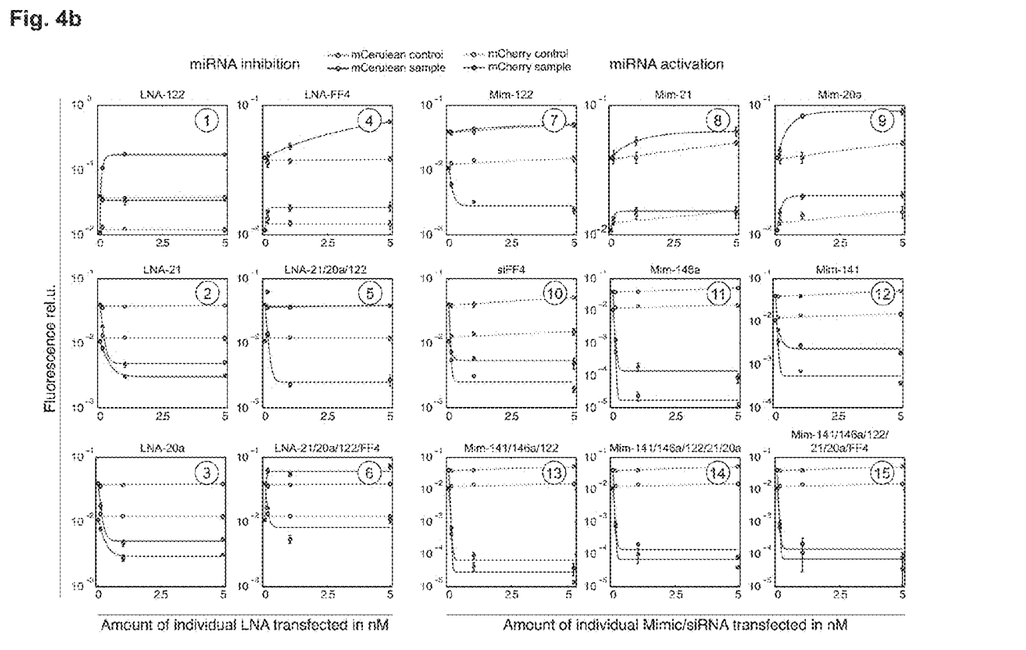

The 15 states used above to characterize the circuits represent extreme cases where each marker is either fully induced or fully inactive. Until now all these perturbation were performed with the goal of exploring the dynamic range of the system and therefore saturating amount of LNA and mimics were used. In order to better understand circuit sensitivity and find smallest detectable perturbbations, dose-response of both the specific and non-specific readouts were measured using three different concentrations of either LNA or mimics corresponding to the 15 conditions (FIG. 4b). Three major conclusions can be drawn from the data. First, specific interactions can be identified for the entire range of perturbation strength for both up- and down-regulation of miR-122 (plots 1 and 7), and half-maximal response is achieved with very weak perturbations. This showed that the assay is sensitive enough to detect small changes. Second, the does-response curves were much steeper for low markers. This is advantageous, since this precludes balancing of two opposing unspecific effects of the same strength (see above). Lastly, in all non-specific scenarios that also involve miR-122 modulation, (cases 5, 6, 13-15), the non-specific reporter is strongly affected as well. With exiting assays these scenarios would be misinterpreted as specific hits. This conclusively proves that the multi-module assay of the present invention is capable of detecting and excluding these false-positive hits.

Small Molecule Library Screen

Figure 5B:
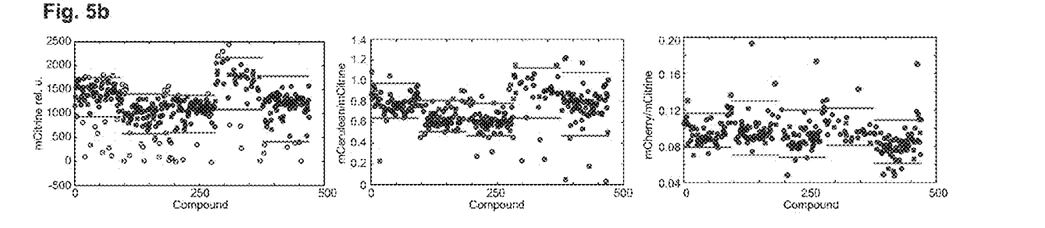
FIG. 5 illustrates the screening of a compound library.

Once the assay was optimized and characterized a pilot small molecule screen was performed. 361 compounds from the NIH Clinical Collections 1 & 2 were tested, which have to the best of knowledge not been screened for miR-122 activity before. The cells were transiently batch-transfected and the performance of the compounds was assayed in triplicates, applying t-test statistics for hit identification (FIG. 5a). Here quantitative data were obtained using image analysis, which showed excellent correlation with flow cytometry data. Assuming that most of the compounds do not show any activity (50), all the samples derived from a given compound plate were used as the reference distribution reflecting unperturbed circuit readouts, and the triplicates measured with individual drugs against this distribution were compared. A p-value cut-off of p<0.1 was defined for compounds to be excluded from further analysis based on changes in gene expression module readout mCitrine. 34.1% percent of the compounds fell into this category, mostly due to effects on cell health as confirmed by additional visual inspection. For further exclusion based on non-specific RNAi module readout, normalized mCerulean, the same cut-off value of p<0.1 was applied, while a p<0.01 cut-off was used for hit identification for the specific module output, normalized mCherry. Based on these criteria 10 hits were identified, which corresponds to a hit rate of 2.8%, and excluded 26.0% of the total number of compounds as potential non-specific RNAi modulators (FIG. 5b).

REFERENCES CITED IN THE EXPERIMENTAL SECTION

1. Rinaudo, K. et al. A universal RNAi-based logic evaluator that operates in mammalian cells. Nat Biotech 25, 795-801 (2007).
2. Xie, Z., Wroblewska, L., Prochazka, L., Weiss, R. & Benenson, Y. Multi-Input RNAi-Based Logic Circuit for Identification of Specific Cancer Cells. Science 333, 1307-1311 (2011).
3. Nakabayashi, H., Taketa, K., Miyano, K., Yamane, T. & Sato, J. Growth of Human Hepatoma Cell Lines with Differentiated Functions in Chemically Defined Medium. Cancer Research 42, 3858-3863 (1982).
4. Lohmann, V. et al. Replication of Subgenomic Hepatitis C Virus RNAs in a Hepatoma Cell Line. Science 285, 110-113 (1999).
5. Coulouarn, C., Factor, V. M., Andersen, J. B., Durkin, M. E. & Thorgeirsson, S. S. Loss of miR-122 expression in liver cancer correlates with suppression of the hepatic phenotype and gain of metastatic properties. Oncogene 28, 3526-3536 (2009).
6. Kutay, H. et al. Downregulation of miR-122 in the rodent and human hepatocellular carcinomas. Journal of Cellular Biochemistry 99, 671-678 (2006).
7. Deal watch: GSK invests in targeting microRNA for the treatment of hepatitis C. Nat Rev Drug Discov 9, 350-350 (2010).
8. Landgraf, P. et al. A Mammalian microRNA Expression Atlas Based on Small RNA Library Sequencing. Cell 129, 1401-1414 (2007).
9. Mangan, S. & Alan, U. Structure and function of the feed-forward loop network motif. Proceedings of the National Academy of Sciences of the United States of America 100, 11980-11985 (2003).
10. Zhang, J.-H., Chung, T. D. Y. & Oldenburg, K. R. A Simple Statistical Parameter for Use in Evaluation and Validation of High Throughput Screening Assays. Journal of Biomolecular Screening 4, 67-73 (1999).

The invention claimed is:
1. A method for identifying miRNA (microRNA)-modulating compounds, the method comprising:
    (A) providing a cell comprising:
        (i) at least one miRNA-specific module comprising a promoter sequence operably linked to at least one miRNA target sequence of interest and a nucleic acid sequence encoding a first reporter product;
        (ii) at least one non-specific RNAi module comprising a promoter sequence operably linked to a nucleic acid sequence encoding a second reporter product operably linked to:
            (a) two or more target sequences for endogenous miRNA markers that may be modulated by off-target effects of a miRNA-modulating compound, and that are characterized by first expression levels in the cell in the absence of a miRNA-modulating compound, and
            (b) at least one target sequence for a signal integrating miRNA, wherein the activity of the signal integrating miRNA depends on at least one of:
                the activity of the two or more endogenous miRNAs that may be modulated by off-target effects of a miRNA-modulating compound, and that are characterized by second expression levels in the cell in the absence of a miRNA-modulating compound that are higher than the first expression levels of the endogenous miRNA markers of (a),
                on the activity of the RNA interference pathway in the cell, or both,
    (B) contacting the cell of step (A) with a compound of interest under physiological conditions, and
    (C) detecting:
        (1) specific miRNA effects of the compound of interest on the miRNA-specific module (i) based on changes in the expression of the first reporter product, and
        (2) off-target and systemic RNAi effects of the compound of interest on the non-specific RNAi module (ii) based on changes in the expression of the second reporter product.
2. The method according to claim 1, wherein the at least one non-specific RNAi module (ii) comprises:
    a promoter sequence operably linked to two or more target sequences for a first group of endogenous non-specific miRNAs markers with baseline expression levels in the cell, and
    (I) at least one target sequence for a signal integrating miRNA, wherein the activity of the signal integrating miRNA depends on the activity of the one or more target sequences for a second group of endogenous non-specific miRNAs markers with baseline expression levels in the cell, and
    (II) a nucleic acid sequence that encodes a second reporter product or that is operably linked to a second reporter product.
3. The method according to claim 1, wherein the first, and second reporter products are different.
4. The method according to claim 1, wherein the promoters in any of modules (i) and (ii) are different.
5. The method according to claim 1, wherein the non-specific RNAi module (ii) comprises two or more target sequences for endogenous miRNAs expressed at different expression levels.
6. The method according to claim 1, wherein the non-specific RNAi module (ii) comprises one or more target sequences for endogenous miRNAs selected from the group of first expression level target sequences miR-200c, 145, 141, 375, 146a and/or from the group of second expression level target sequences miR-21, 17, 130a and 20a.
7. The method according to claim 1, wherein the non-specific RNAi module (ii) comprises at least one target sequences for endogenous miRNAs selected from the group of first expression level target sequences miR-141 and miR-146a and/or from the group of second expression level target sequences miR-21 and miR-20a.

8. The method according to claim 1, wherein the cell is a disease model cell, a cancer cell, an HCV model cell, a HuH-7 cell.

9. The method according to claim 1, wherein the specific miRNA target sequence of interest in the at least one miRNA-specific module (i) binds specifically to miR-122.

10. The method according to claim 1, wherein at least one of the reporter products in the miRNA-specific module (i), and the non-specific RNAi module (ii) is a fluorescent protein or luciferase, preferably.

11. The method according to claim 10, wherein the fluorescent protein is selected from the group consisting of mCitrine fluorescent protein, mCherry fluorescent protein, ZsYellow fluorescent protein, and mCerulean fluorescent protein.

12. The method according to claim 1, wherein the promoters in any of modules (i) and (ii) are the same.

13. The method of claim 1, wherein:
the cell further comprises (iii) at least one gene expression module comprising a promoter sequence operably linked to a nucleic acid sequence encoding a third reporter product; and the method further comprises in (C): detecting non-specific effects of the compound of interest on the gene expression module (iii) based on changes in the expression of the third reporter product.

14. The method according to claim 13, wherein the first, second and third reporter products are different.

15. The method according to claim 13, wherein the promoters in any of modules (i) to (iii) are different.

16. The method according to claim 13, wherein the promoters in any of modules (i) to (iii) are the same.

17. The method according to claim 13, wherein at least one of the reporter products in the miRNA-specific module (i), and the non-specific RNAi module (ii) and/or the gene expression module (iii) is a fluorescent protein or luciferase.

18. The method according to claim 17, wherein the fluorescent protein is selected from the group consisting of mCitrine fluorescent protein, mCherry fluorescent protein, ZsYellow fluorescent protein, and mCerulean fluorescent protein.

* * * * *